（12）United States Patent
Yelin

(10) Patent No.: US 11,033,209 B2
(45) Date of Patent: Jun. 15, 2021

(54) HEMOGLOBIN MEASUREMENT FROM A SINGLE VESSEL

(71) Applicant: TECHNION RESEARCH & DEVELOPMENT FOUNDATION LIMITED, Haifa (IL)

(72) Inventor: Dvir Yelin, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 318 days.

(21) Appl. No.: 15/779,604

(22) PCT Filed: Nov. 30, 2016

(86) PCT No.: PCT/IL2016/051286
§ 371 (c)(1),
(2) Date: May 29, 2018

(87) PCT Pub. No.: WO2017/094010
PCT Pub. Date: Jun. 8, 2017

(65) Prior Publication Data
US 2018/0344228 A1 Dec. 6, 2018

Related U.S. Application Data

(60) Provisional application No. 62/260,978, filed on Nov. 30, 2015.

(51) Int. Cl.
A61B 5/1455 (2006.01)
A61B 5/00 (2006.01)
A61B 5/145 (2006.01)

(52) U.S. Cl.
CPC ........ A61B 5/14551 (2013.01); A61B 5/0075 (2013.01); A61B 5/14535 (2013.01);
(Continued)

(58) Field of Classification Search
CPC ............ A61B 5/14551; A61B 5/14545; A61B 5/0075; A61B 5/0077; A61B 5/0068; A61B 5/441
See application file for complete search history.

(56) References Cited

U.S. PATENT DOCUMENTS 5,692,503 A    12/1997  Kuenstner
5,722,398 A *   3/1998  Ishihara ............... A61B 5/1455
                                                 600/322
(Continued)

FOREIGN PATENT DOCUMENTS

DE    4433827 A1    3/1996
EP    0875201 B1   11/1998
(Continued)

Primary Examiner — Eric F Winakur
Assistant Examiner — Abid A Mustansir
(74) Attorney, Agent, or Firm — The Roy Gross Law Firm, LLC; Roy Gross

(57) ABSTRACT

A system and method to measure blood oxygenation levels and total hemoglobin on individually selected blood vessels, to provide a representation of the subject condition and of tissue perfusion that may be used for diagnosing specific tissue conditions. Reflection spectra from individual blood vessels or a collection of vessels are measured by using wide-field imaging for selecting target vessels and a narrow-field confocal detection system to enable measuring local blood oxygenation and hemoglobin. Optical fibers may be used to illuminate the target vessel and to detect light diffusively reflected therefrom. The reflection spectra may be analyzed in a spectrometer to extract the ratio of the deoxy- to oxyhemoglobin and to determine their absolute concentration for computing total hemoglobin levels. An alternative implementation uses image processing on camera images of a blood vessel, generated at an isosbestic wavelength of the deoxy- and oxyhemoglobin, and optionally also at neighboring wavelengths.

17 Claims, 8 Drawing Sheets

(52) U.S. Cl.
CPC ........... *A61B 5/0068* (2013.01); *A61B 5/0077* (2013.01); *A61B 5/441* (2013.01)

(56) References Cited

U.S. PATENT DOCUMENTS

| | | | | |
|---|---|---|---|---|
| 5,974,338 | A | * 10/1999 | Asano | ................ A61B 5/14535 600/322 |
| 2004/0106163 | A1 | 6/2004 | Workman et al. | |
| 2005/0033185 | A1 | 2/2005 | Danen | |
| 2006/0100524 | A1 | * 5/2006 | Lucassen | ............... G01N 21/65 600/476 |
| 2007/0219439 | A1 | 9/2007 | Vilser et al. | |
| 2008/0255457 | A1 | 10/2008 | Khoobehi et al. | |
| 2010/0317941 | A1 | 12/2010 | Kuhn et al. | |
| 2011/0261321 | A1 | 10/2011 | Ramella-Roman et al. | |
| 2013/0324815 | A1 | 12/2013 | Jian et al. | |

FOREIGN PATENT DOCUMENTS

| | | | | |
|---|---|---|---|---|
| WO | 0006017 | A1 | 2/2000 | |
| WO | 2006129740 | A1 | 12/2006 | |
| WO | WO-2013108209 | A1 * | 7/2013 | ........... A61B 5/0066 |
| WO | 2014042773 | A1 | 3/2014 | |
| WO | 2014204841 | A1 | 12/2014 | |

* cited by examiner

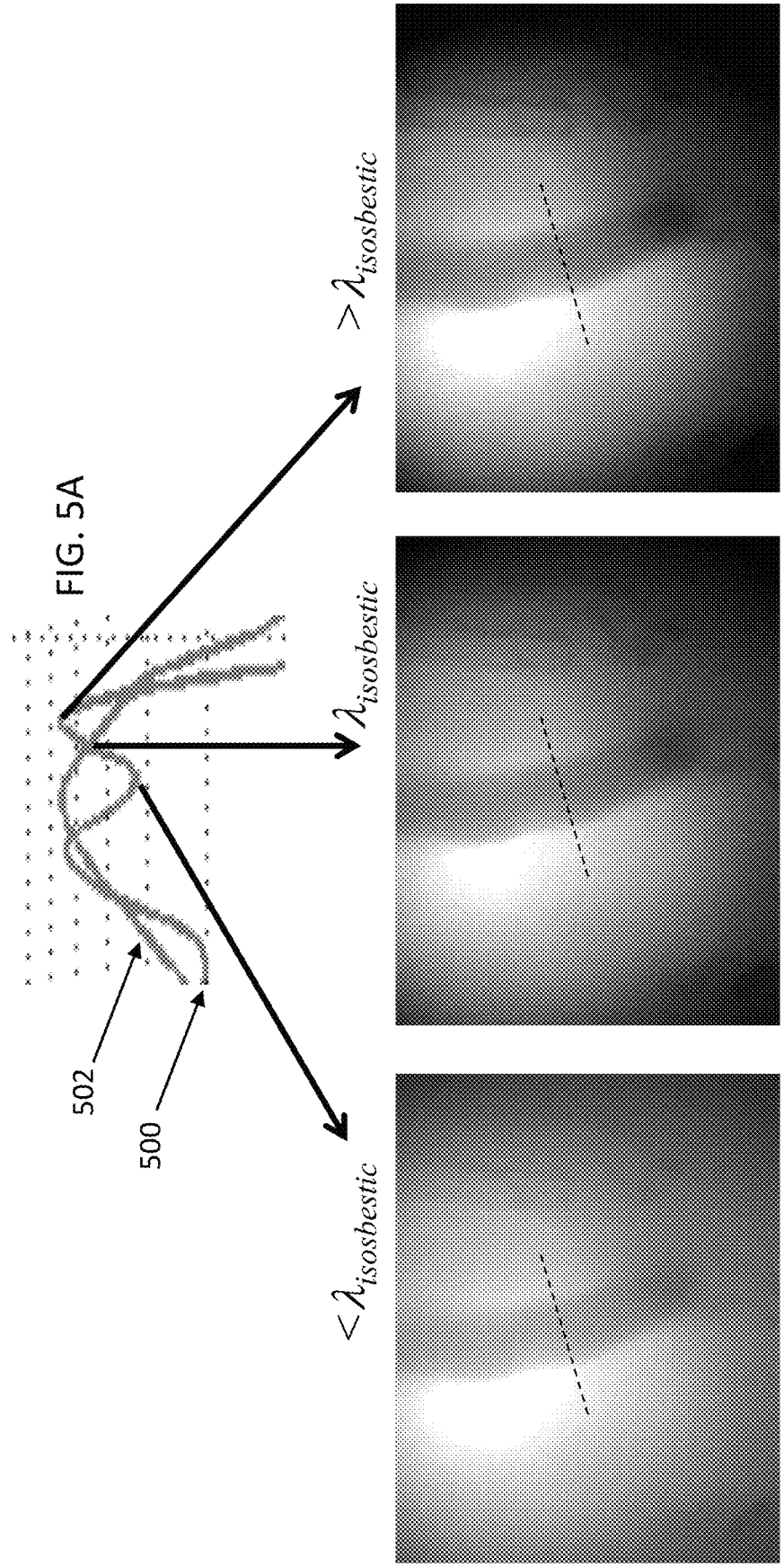

HEMOGLOBIN MEASUREMENT FROM A SINGLE VESSEL

RELATED APPLICATIONS

This application is a National Phase of PCT Patent Application No. PCT/IL2016/051286 having International filing date of Nov. 30, 2016, which claims the benefit of priority of U.S. Patent Application No. 62/260,978 filed on Nov. 30, 2015. The contents of the above applications are all incorporated by reference as if fully set forth herein in their entirety.

FIELD OF THE INVENTION

The invention relates to the field of pulse oximetry, especially that providing information on hemoglobin levels in individual blood vessels.

BACKGROUND

Hemoglobin is the metalloprotein that carries the oxygen in the red blood cells, and makes up about 97% of the dry content of these cells. A single Hemoglobin molecule can bind up to four oxygen molecules present in the lungs for releasing in the tissues.

Several methods exist for measuring blood oxygen saturation. The arterial blood gas (ABG) test uses blood collected directly from an artery into a vacuum tube that maintains the oxygenation level. The gas content in the collected blood sample is then tested to measure arterial oxygen tension (PaO2). Pulse oximetry measures the arterial oxygen saturation optically by exploiting the different absorption spectra of hemoglobin and oxyhemoglobin, indicated in FIG. 1, as well as the pulsatile nature of the arterial flow. An advantage of pulse oximetry is its noninvasiveness, which both reduces risk of infection and other complications arising from invasive techniques, and eliminates pain.

Typically, pulse oximetry measures the absorption of two or more optical wavelengths by the red blood cells. Light at two wavelength bands may be transmitted through the patient's finger, or ear lobe, illuminating tissue lying therebelow, such as blood vessels, which scatter the light. The scattered light is measured as it leaves the tissue to indicate oxygenation levels. The first band, typically selected at approximately 800 nm, where oxy- and deoxy-hemoglobin have approximately equal absorption, serves as a reference to the total amount of hemoglobin in the optical path. The second band, typically in the region of 950 nm, may be absorbed very differently by the two hemoglobin forms, and may be used to indicate the oxygen saturation level within the blood.

While measuring the level of oxygenation is important in arterial blood for assessing heart and lung function, it may also be used to measure blood oxygenation in capillaries, which are the primary location for the exchange of oxygen and carbon dioxide between the blood and the tissue. For example, such measurement could provide information of tissue conditions and hypoxia, and serve as a tool to measure local tissue viability during invasive surgery. In addition, knowledge of blood oxygenation in veins is an important clinical parameter; however, it does not provide direct information on oxygen perfusion into the tissue, as large portion of the blood are transferred directly from the arteries to the veins without passing through the capillary network. Thus, venous blood oxygenation is not always an accurate indication on tissue perfusion.

Conventional pulse oximetry performs measurements on light diffused within the tissue in order to assess the arterial blood oxygenation levels. Thus, the optical measurement obtained by these methods often combines the absorption of many blood vessels, such as large arteries, arterioles, arterial capillaries, venous capillaries, venules, and large veins. To separate the different blood oxygenation levels of the different types of vessels, pulse oximetry often relies on the temporal pulsation of the arterial blood volume, allowing the subtraction of the constant background light attenuation. Hence, pulse oximetry is limited in that it measures blood oxygenation levels in pulsed vessels only, i.e. arterial vessels only, such that there exists a need for a measurement system that enables the blood oxygenation levels to be measured also in venous vessels, or in groups of vessels having similar physiological properties but not limited to any specific type.

Prior art optical methods mainly concentrate on determination of the oxygenation levels in blood vessels tested based on the measured ratio of oxyhemoglobin to deoxyhemoglobin. Such measurements are described in German Patent Application published as DE 4433827 A1, by Friedrich Schiller University, Jena, for (freely translated) "Method and apparatus for measuring substance parameters in material layers, especially calibration-free, in-vivo, oxygen saturation in optically accessible blood containing structures", and in International Patent Application published as WO 2006/129740 by Olympus Corporation et al., for "Hemoglobin observing device and hemoglobin observing method".

However, the total hemoglobin level is also an important parameter necessary for assessing the patient's general health status. The main challenge in measuring hemoglobin concentration is the need to measure an absolute absorption parameter, in contrast to the above mentioned blood oxygenation parameters, that require measurement of only the ratio between absorption spectra. There therefore exists a need for simple, non-invasive optical methods and apparatus for making in-vivo measurements of the total hemoglobin level in blood vessels.

The foregoing examples of the related art and limitations related therewith are intended to be illustrative and not exclusive. Other limitations of the related art will become apparent to those of skill in the art upon a reading of the specification and a study of the figures.

SUMMARY

A system and method are disclosed herein to measure blood oxygenation and total hemoglobin on individually selected blood vessels, to provide a representation of tissue perfusion that may be used for diagnosing specific tissue conditions. Reflection spectra from individual blood vessels can be measured by using wide-field illumination and a narrow-field confocal detection system to enable high resolution selection and focus onto a target vessel for measuring blood oxygenation and hemoglobin. Optical fibers may be used to illuminate the target vessel and to detect light reflected therefrom.

The following embodiments and aspects thereof are described and illustrated in conjunction with systems, tools and methods which are meant to be exemplary and illustrative, not limiting in scope.

There is thus provided in accordance with an exemplary implementation described in this disclosure, a method for measuring total hemoglobin concentration in a blood vessel, comprising:

(i) illuminating a bodily tissue containing the blood vessel, (ii) generating images of the blood vessel and its surrounding tissue at a first wavelength in the region of an isosbestic wavelength of oxyhemoglobin and deoxy-hemoglobin, (iii) determining at the first wavelength, the comparative imaged intensities of the blood vessel and of the surrounding tissue, (v) estimating the optical path length of the illumination through the vessel, and (vi) using the estimated optical path length and the comparative imaged intensities of the blood vessel and of the surrounding tissue to determine the total hemoglobin concentration in the blood flowing in the blood vessel. In such a method, the step of estimating the optical path length of the illumination through the vessel may be obtained after determining the size of the vessel from at least one of the generated images.

The above described method may further comprise:

(vii) generating images of the blood vessel and its surrounding tissue at at least one additional wavelength in proximity to the first wavelength, (viii) determining the comparative imaged intensities of the blood vessel at the first wavelength and at the at least one additional wavelength in proximity thereto, and (ix) using the comparative imaged intensities of the blood vessel to determine the oxygen absorption level in the blood. In such a case, the at least one additional wavelength may be a range of multiple wavelengths.

In any of the above described methods, the images of the blood vessel and its surrounding tissue may be obtained from a camera system, or from a narrow field confocal microscope system. Additionally, the first wavelength images may be generated by illuminating at the first wavelength, or by imaging at the first wavelength.

According to yet further implementations of the present disclosure, there is further provided a system for measuring total hemoglobin concentration in a blood vessel, comprising:

(i) a light source configured to illuminate the blood vessel and its surrounding tissue, (ii) a camera configured to generate images of the blood vessel and its surrounding tissue at a first wavelength in the region of an isosbestic wavelength of oxyhemoglobin and deoxy-hemoglobin, and (iii) a processor configured to:

(a) determine from at least one of the images generated at the first wavelength, the comparative imaged intensities of the blood vessel and of the surrounding tissue, (b) estimate the optical path length of the illumination through the blood vessel, and (c) use the estimated optical path length and the comparative imaged intensities of the blood vessel and of the surrounding tissue to determine the total hemoglobin concentration in the blood flowing in the blood vessel. The estimating of the optical path length of the illumination through the vessel may be obtained after determining the size of the vessel from at least one of the generated images.

According to a further implementation of the described system, the camera may be configured to generate images of the blood vessel and its surrounding tissue at at least one additional wavelength in proximity to the first wavelength, and in addition, the processor may be further configured to (d) determine the comparative imaged intensities of the blood vessel at the first wavelength and at the at least one additional wavelength in proximity thereto, and (e) use the comparative imaged intensities of the blood vessel to determine the oxygen absorption level in the blood. In such a system the at least one additional wavelength may be a range of multiple wavelengths.

In any of the above described systems the light source may be configured to provide wide field illumination. Furthermore, the camera may comprise a confocal microscope system configured to image the blood vessel and its surrounding tissue.

According to additional configurations of the above described systems, the first wavelength images may be generated by illuminating at the first wavelength, or by use of a light source providing illumination at the first wavelength. The first wavelength images may be generated by at least one filter disposed in the optical path of the illumination either before incidence on the blood vessel and its surrounding tissue, or after reflection from the blood vessel and its surrounding tissue.

There are described in the present disclosure, yet further implementations of apparatus, for determining the oxygen level and hemoglobin in at least one blood vessel of a subject, comprising:

(i) a light source configured to illuminate a bodily tissue with a plurality of wavelengths, (ii) a light collector configured to collect light diffusively scattered from the bodily tissue, (iii) a spectrum detector configured to receive the collected light and determine a spectrum corresponding to the collected light, and (iv) a processor configured to determine a blood oxygen absorption level corresponding to the determined spectrum, wherein the light source and the light collector may comprise a confocal detection system having a detection volume such that the detector receives light only from a region containing the at least one vessel of the subject.

In such an apparatus, the at least one blood vessel may be either a single blood vessel or a group of vessels of similar physiological properties. Additionally, the spectrum detector may be a spectrometer.

According to further implementations, the apparatus may further comprise a camera in optical communication with the light collector, and configured to image the bodily tissue using the collected light, thereby allowing the light source and the light collector to be maneuvered onto any of a single selected blood vessel and tissue surrounding the at least one blood vessel. In such a case, the processor should be configured to determine the oxygen absorption level of the at least one blood vessel by analyzing i) a reference spectrum corresponding to the tissue surrounding the at least one blood vessel, wherein the reference spectrum does not include spectral information corresponding to the at least one blood vessel, and ii) a blood vessel spectrum corresponding only to the at least one blood vessel.

The apparatus then may further comprise:

(i) a first fiber coupled to the light source and having a relatively large core, and configured to illuminate the bodily tissue with a widefield beam having an illumination region comparable to the cross-section of the at least one blood vessel, (ii) a detection channel providing the optical communication between the light collector and the camera, thereby providing the camera with collected light having a collection volume corresponding to the widefield beam, and (iii) a second fiber in optical communication with the light collector and coupled to the spectrum detector, wherein the second fiber has core size providing the spectrum detector with collected light having a collection volume that is of the order of the cross-section of the at least one blood vessel. In any of the above described apparatus, the at least one blood vessel may be at least one capillary.

Finally, as an alternative to the above described apparatus implementations, there is further provided an apparatus for determining the oxygen absorption level in a blood vessel of a subject, comprising:

(i) a light source configured to illuminate a bodily tissue with wavelengths at an isosbestic wavelength of oxyhemoglobin and deoxy-hemoglobin, and at wavelengths in proximity thereto, (ii) a camera configured to generate images of the blood vessel and its surrounding tissue at the isosbestic wavelength and at the wavelengths in proximity thereto, and (iii) an image processor configured to
  (a) determine the comparative imaged intensities of the blood vessel at the isosbestic wavelength and at the wavelengths in proximity thereto, and
  (b) determine the oxygen absorption level in the blood vessel from the comparative imaged intensities of the blood vessels determined in step (i).

According to yet further implementations of the present disclosure, there is provided a method for determining the oxygen level and hemoglobin in at least one blood vessel of a subject, comprising:

(i) illuminating a bodily tissue with a plurality of wavelengths, (ii) collecting light diffusively scattered from the bodily tissue, (iii) determining a spectrum corresponding to the received light, and (iv) determining a blood oxygen absorption level corresponding to the determined spectrum, wherein the light source and the light collector may comprise a confocal detection system having a detection volume such that the light collector receives light only from a region containing the at least one blood vessel of the subject. In such a method, the at least one blood vessel may be either a single blood vessel or a group of vessels of similar physiological properties. The single blood vessel may be a capillary.

Additional implementations of the above method may invoke:

(i) imaging the bodily tissue using the collected light, and (ii) directing the light source and the light collector onto any of a single selected blood vessel and tissue surrounding the selected single blood vessel using the images. In either of the previous two methods, the step of determining the blood oxygen absorption level corresponding to the determined spectrum may comprise determining the blood oxygen absorption level of the selected single blood vessel by analyzing i) a reference spectrum corresponding to the tissue surrounding the single blood vessel, wherein the reference spectrum does not include spectral information corresponding to the single selected blood vessel, and ii) a blood vessel spectrum corresponding only to the selected single blood vessel. In such a case, the method may further comprise:

(i) illuminating the bodily tissue with a widefield beam having a point spread function comparable to the width of the selected single blood vessel, (ii) imaging the bodily tissue with collected light having a collection volume corresponding to the widefield beam, thereby maneuvering the light source and light collector in accordance with a resolution associated with the widefield beam, and (iii) providing a spectrum detector with the portion of the collected light having the collection volume that is smaller than the cross-section of the selected single blood vessel, thereby determining the blood oxygen absorption level of the selected single blood vessel.

Finally, as an alternative to the above described methods, there is further provided a method for determining the blood oxygen level and hemoglobin in a blood vessel of a subject comprising:

(i) illuminating a bodily tissue with wavelengths at an isosbestic wavelength of oxyhemoglobin and deoxy-hemoglobin, and at wavelengths in proximity thereto, (ii) generating images of the blood vessel and its surrounding tissue at the isosbestic wavelength and at the wavelengths in proximity thereto, (iii) determining the comparative imaged intensities of the blood vessel at the isosbestic wavelength and at the wavelengths in proximity thereto, and (iv) using the comparative imaged intensities of the blood vessel to determine the oxygen absorption level in the blood.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 5A-G show a method to determine oxygenation of a blood vessel, in accordance with another implementation of the present disclosure.

DETAILED DESCRIPTION

Figure 1:
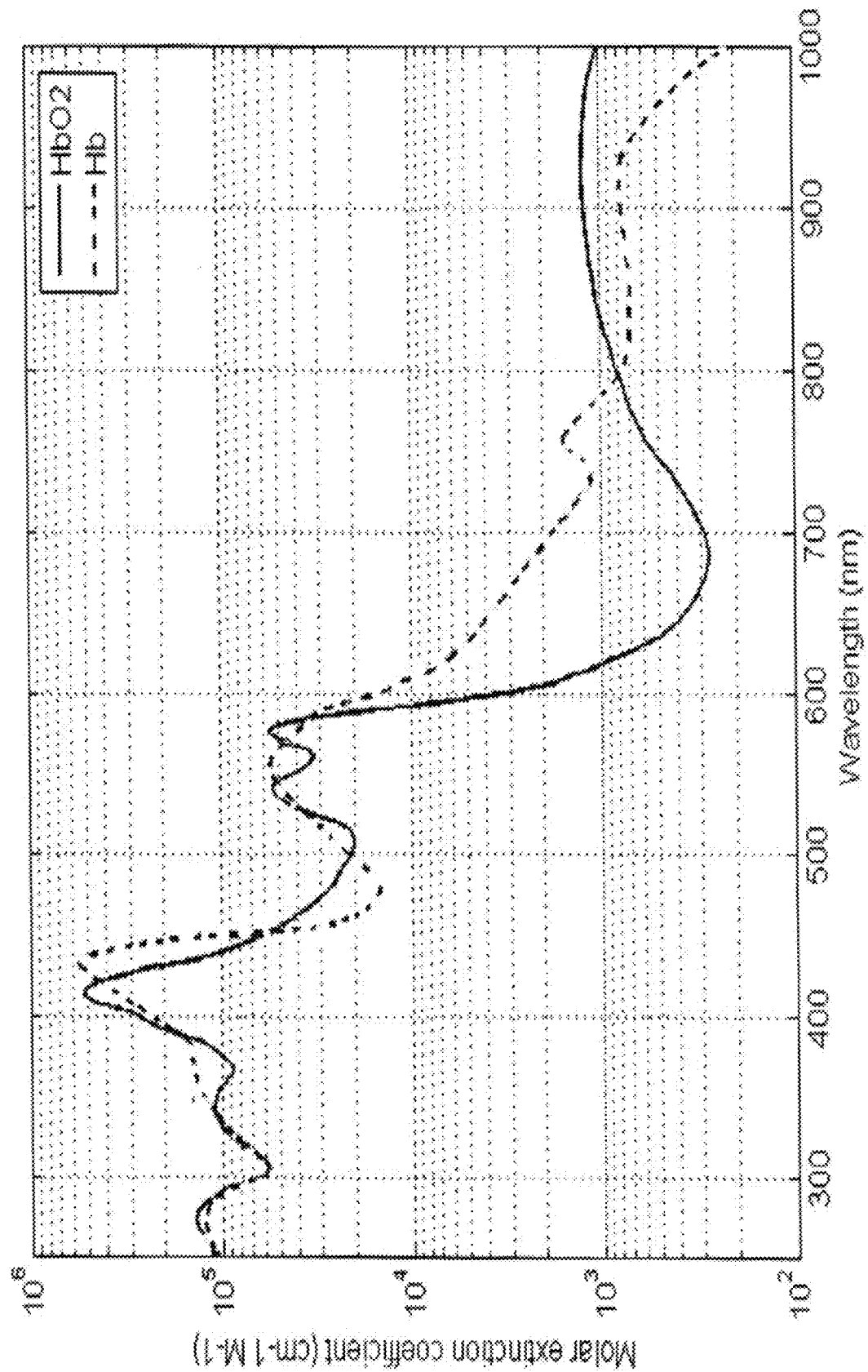
FIG. 1 shows absorption spectra for hemoglobin and oxyhemoglobin.

Reference is first made to FIG. 1, which shows the absorption spectra for hemoglobin and oxyhemoglobin from the visible through the near infra-red region, showing the characteristic isosbestic points, one in the infra-red at approximately 805 nm, and others in the visible in the 500 to 600 nm region, such as 569 and 586 nm.

Figure 2A:
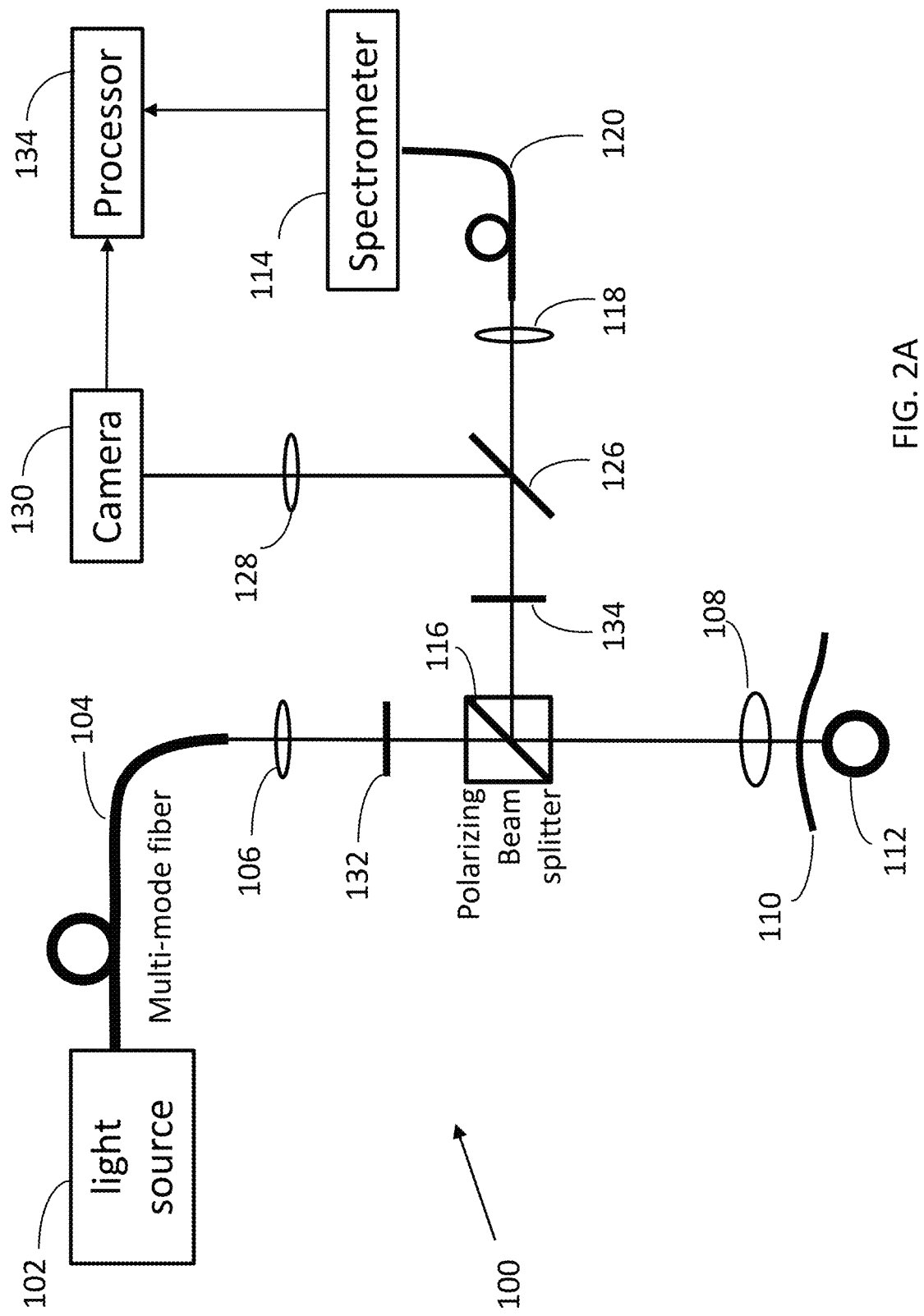
FIG. 2A shows an exemplary implementation of an optical apparatus for measuring reflection spectra from individual blood vessels.

Reference is now made to FIG. 2A, which illustrates an exemplary optical apparatus 100 for measuring reflection spectra from individual blood vessels, in accordance with one implementation of the systems described in this disclosure. A light source 102 coupled to a multimode fiber 104 may emit broadband light which is channeled through fiber 104 and collimated by a lens 106. The collimated light may be projected via an objective lens 108 onto a tissue surface 110 covering a blood vessel 112.

Optical apparatus 100 generates a confined illumination distribution over blood vessel 112. For example, one or more parameters of optical apparatus 100 may be selected to produce an illumination beam having dimensions in the order of the width of vessel 112, or slightly larger. Alternatively, the beam illuminates a larger region that contains a plurality of vessels having similar physiological characteristic, for example arterioles, or venules or capillaries. Fiber 104 may be selected to have a relatively large core, such as a multimode fiber having a core in the order of 50 micrometers ($\mu$m) and the parameters of lenses 106, and 108 may be selected accordingly, to produce the desired illumination beam dimensions.

Objective lens 108 may collect light scattered by illuminated tissue 110. A beam splitter 116 directs the collected light to a spectrometer 114 via a coupling lens 118 and a single-mode fiber 120. Fiber core 120 may be selected to have a relatively small diameter, such as in the order of 5 $\mu$m, resulting in a light collection region that is smaller than the illumination region. The resulting point-spread function (PSF) of the combined illumination and collection optical paths may have dimensions that are comparable to the cross-section of the target vessel or group of vessels 112, and as a result, may allow obtaining a spectral measurement from the vessels 112 without including spectral information from nearby and/or deeper vessels. The apparatus 100 may most conveniently be constructed as a single readily maneuverable unit. Alternatively, the optical source 102, the spectrometer 114, the camera 130, the processor 134, and any display unit (not shown) may be incorporated into a separate static module, connected to a moveable scanning optical head by means of the fiber optical and electronic links, or any other suitable arrangement may be used.

Figure 2B:
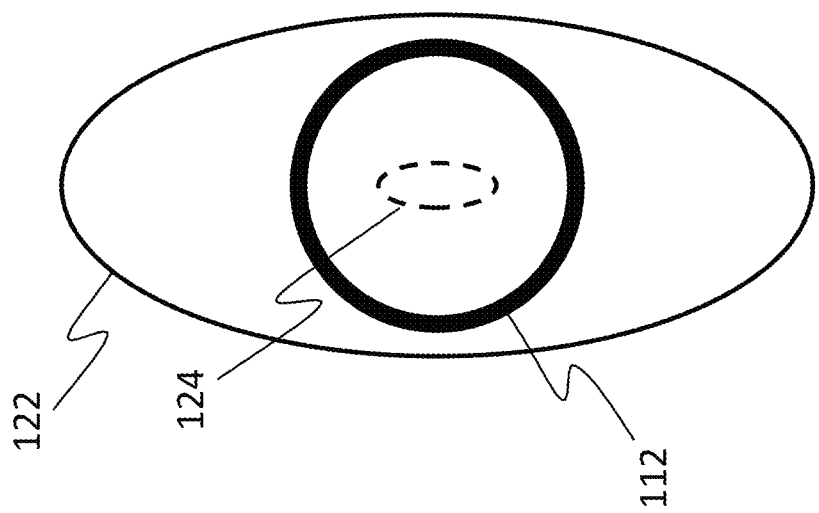
FIG. 2B shows an example of a zoomed in view of a blood vessel cross section illuminated and measured with the apparatus of FIG. 2A.
Figure 2C:
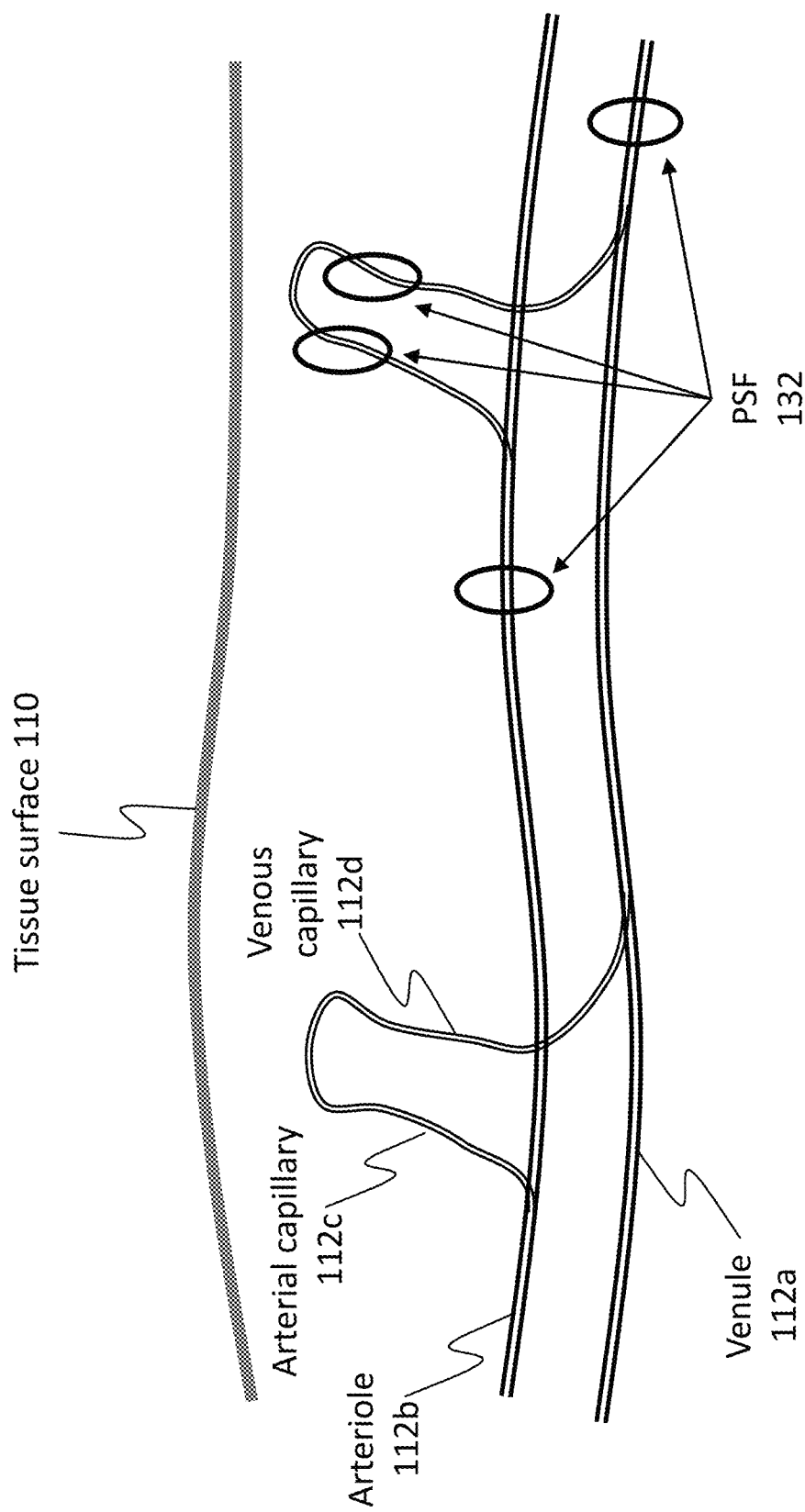
FIG. 2C shows multiple different types of blood vessels beneath the tissue surface illuminated separately to allow collecting individual spectra.

Referring to FIG. 2B, a zoomed in view of vessel 112 is shown. The representation 122 of the illuminated region produced by optical apparatus 100 should have a width that is comparable to or slightly larger than the width of vessel 112, whereas the collection region 124 of optical apparatus 100 should have a width that is smaller than the width of vessel 112, to prevent the inclusion of spectral information from tissue outside of vessel 112. This is indicated in FIG. 2C which shows multiple different types of blood vessels 112: a venule 112a, an arteriole 112b, an arterial capillary 112c, and a venous capillary 112d located beneath the tissue surface 110, illuminated separately to allow collecting individual spectra corresponding to each blood vessel. PSF representations 132 are shown sized to illuminate the blood vessels individually, allowing spectral information to be exclusively collected from each blood vessel for separate analysis. However, other implementations may be used in which the illumination and the detection systems can function on a group of vessels closely located having similar physiological properties.

An imaging arrangement is provided, having sufficient resolution to limit the collection of light only to that diffused from the vessel, and to enable visualization for selecting the blood vessel and spectral measurement of that reflected light. Referring back to FIG. 2A, the imaging channel comprising a beam splitter 126 coupled to a lens 128 to image the focal plane of objective lens 108 onto a camera 130. Optionally, two crossed-polarizers 132 and 134 may be provided along the optical path to reduce surface scattering and glare for reducing image background and noise.

To improve accuracy and reduce measurement error, a reference spectrum may be measured at a location close to the target vessel, and used to calibrate optical apparatus 100. Camera 130 may be used to identify vessel 112 to allow maneuvering optical apparatus 100 to target the illuminating beam sequentially on vessel 112 or on a surrounding reference tissue sample for spectral analysis. For example, the apparatus or part of it, may be maneuvered to enable camera 130 to collect either a reference spectrum from tissue surrounding vessel 112, or a spectrum exclusively from vessel 112. The collected spectra may be provided to a processor 134 for analysis. Additionally or alternatively, one or more of the images captured by camera 130 may be provided to processor 134 for analysis accordingly, as described below in the implementation of FIGS. 5A-5G. Processor 134 may render any of the images, spectral information, and/or determined absorption levels on a display 136.

Figure 3A:
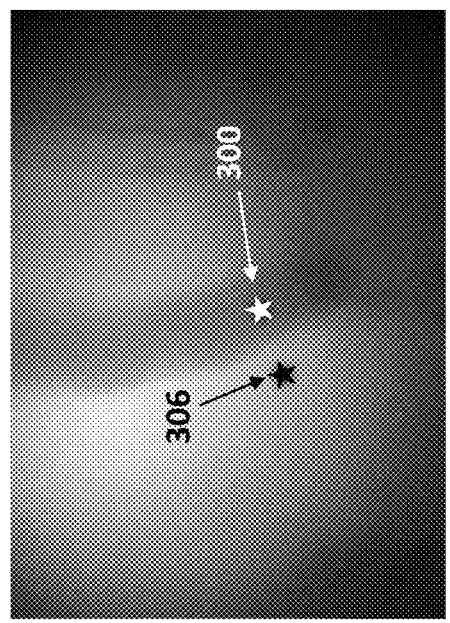
FIGS. 3A-C, show typical images of capillaries and surrounding tissue on the lip of a subject.
Figure 3B:
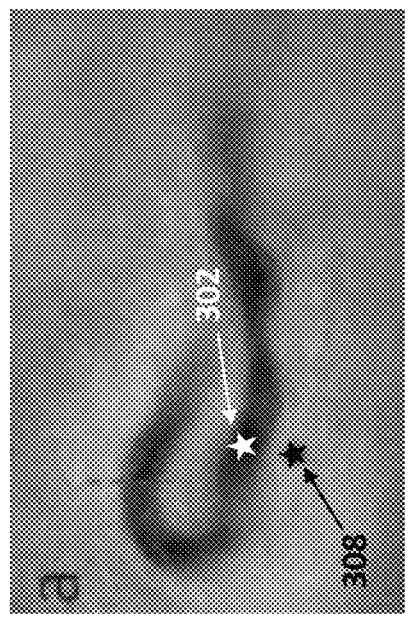
Figure 3C:
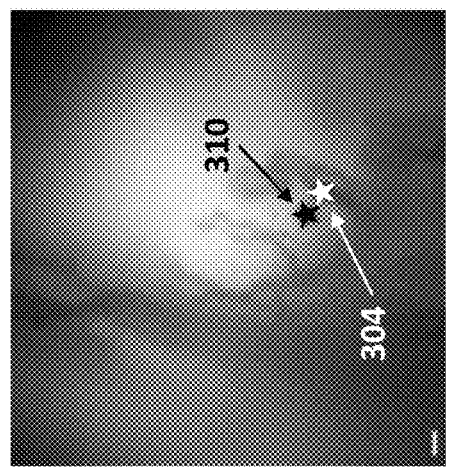

Referring to FIG. 3A-C, typical images of capillaries on the lip of a subject are shown, where the vessels appear as dark lines on a bright background due to the high absorption of blood compared to the surrounding tissue. White stars 302, 304, and 306 indicate locations inside vessel 112, and black stars 308, 310, and 312 indicate locations outside vessel 112. Spectra corresponding to location pairs (300, 306), (308, 302), and (304, 310) may be recorded and provided to processor 134, to determine absorption levels using any of the methods described below.

Figure 4:
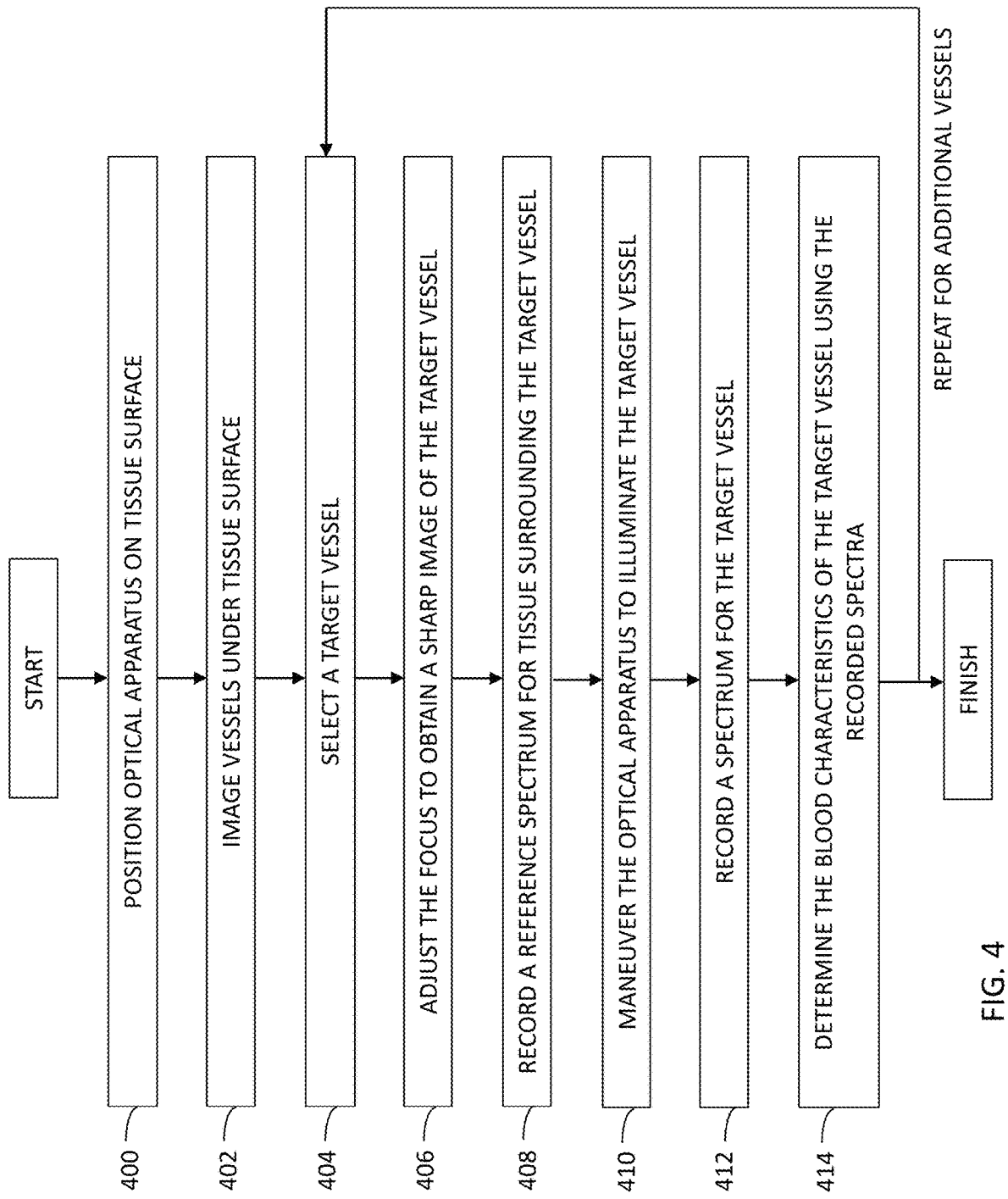
FIG. 4 shows a flowchart of an exemplary method for measuring blood oxygenation levels using the system of FIG. 2A.

Referring to FIG. 4, a flowchart is shown of one method for measuring blood oxygenation levels. The optical apparatus is positioned at the surface of a bodily tissue (Step 400), such that the region of interest is illuminated. The vessels lying under the bodily tissue are imaged using the camera (Step 402), and a target vessel is selected (Step 404), and the focus is adjusted to obtain a sharp image of the target vessel (Step 406). The device is now maneuvered to illuminate surrounding tissue near, but not including the target vessel, and a reference spectrum emitted by the surrounding tissue is recorded by the spectrometer (Step 408). The optical apparatus is now maneuvered to orient the illumination onto the target vessel itself in both the lateral and axial (focus) dimensions (Step 410), and the spectrum emitted from the target vessel is recorded by the spectrometer (Step 412). The blood oxygenation level corresponding to the target vessel is determined by analyzing the recorded target vessel spectrum as compared with the recorded surrounding tissue spectrum (Step 414). Steps 410-414 may be repeated for additional blood vessels in proximity to the surrounding tissue corresponding to the reference spectrum.

In some implementations, light source 102 may produce broadband light, or alternatively, light comprising several wavelength bands. As stated in the Background Section, conventional pulse oximetry generally uses wavelengths at approximately 800 nm for the reference measurement, and a second band, typically in the region of 950 nm, for determining the oxyhemoglobin level. The latter wavelength range is used for conventional oximetry measurements because that is a spectral region having a large difference between the deoxy-hemoglobin absorbance and the oxyhemoglobin absorbance. In that spectral region, the light is weakly scattered by tissue and fairly weakly absorbed, but that the low absorption is not necessarily problematic for conventional oximetry measurements since measurements are taken over a comparatively large tissue and blood volume, typically of several millimeters cross section, such that there is a satisfactory transmitted signal. However, using the methods and systems of the present disclosure for imaging small individual blood vessels, which could be only tens of microns in diameter, the diffusely reflected optical intensity in that spectral region is very small because of the low absorption in the vessel, making it difficult to detect the diffusively reflected spectra in such a low optical attenuation medium. Furthermore, since the measurements are made on blood vessels near the surface of the subject's tissue, it is important that the incident light does not penetrate too deeply into the tissue without attenuation, so that the absorption in the imaged blood vessels can be successfully measured. Therefore, in the presently described system, it is more advisable to use a spectral region where the optical absorbance and scattering is higher, provided that the difference in absorbance between the oxy- and the deoxy-hemoglobin is sufficient to enable differentiation between them. Consequently, for the differentiating measurement, a detection wavelength in the 500 to 600 nanometer range is used, where the absorbance is greater by almost two orders of magnitude than in the near infra-red 700 to 900 nm region. Although the differential absorbance in the 500 to 600 nm region is smaller than in the infra-red, the greatly increased overall absorption level enables a better signal-to-noise ratio to be achieved for small size measurements of individual blood vessels. Spectrometer 114 may optionally be replaced by a simpler wavelength discrimination arrangement, such as a combination of a dichroic mirror or filters, with one or more detectors, to measure several predefined spectral bands. Oxygenation levels may be measured by fitting the measured spectrum to a linear combination of the absorption curves for oxy- and deoxy-hemoglobin, or alternatively by measuring the relative absorptions of different spectral bands, as in pulse oximetry. The volume of the blood vessels from which the spectra are measured may be estimated from the image of the camera. Consequently, the average optical path length of the diffusively scattered light within the vessel may be estimated. Using these parameters, the total hemoglobin levels within the vessel may be computed by adding the computed levels of deoxyhemoglobin and oxyhemoglobin. The level of carbon monoxide may also be measured using this approach by measuring the spectral characteristics of carboxyhemoglobin.

In some implementations, off-axis illumination may be used to provide dark field illumination, to improve image quality of the imaging channel, and resulting in less glare from the tissue surface and enhanced image contrast. Optionally, the widefield-imaging wavelength illumination beam may be separated from the measurement beam using dichroic mirrors.

Although the above described systems and methods use a large area illumination beam and a small area imaging field of view, it is also possible for the optical setup of the spectral measurement to be reversed by providing a single-mode fiber for illuminating a relatively small spot on the tissue, and a relatively larger-core multimode fiber for collecting the scattered light, resulting is the same overall system PSF as shown in FIG. 2B while providing a higher illumination intensity. However, care must then be taken to ensure that the high incident intensity does not cause tissue damage, and a larger illumination spot may be advantageous since it allows taking measurements using higher optical power without damaging the tissue.

Optionally, the optical fibers used for the illumination and collection channels may be replaced by a small-area light source and/or detector, with spatial filtering, in a free-space optical setup (not shown).

Reference is now made to FIGS. 5A to 5G, which illustrate an alternative method of determining the total hemoglobin and the oxygenation levels within blood vessels, only using the imaging functions of the apparatus of FIG. 2A, and without the need for focusing the incident light or the need for spectrometric measurements. Measurements are taken at the isosbestic points and at wavelengths close to it. In this method, the difference in reflectance (or absorbance) between the vessel and its nearby tissue is determined by performing image processing on images of the blood vessel, and using the relative intensities of the light diffusively reflected from the blood vessel and its surrounding tissues, in order to extract information relating to the illumination absorption. These measurements assume that the light absorbance in the tissue surrounding the vessel does not change appreciably with small changes in wavelength around the isosbestic point, and that the surrounding tissue can therefore be used as a normalizing factor for compensating for random changes in the brightness or contrast of the images captured at the isosbestic point and its neighboring measurement points. By this means, the intensities of the optical signals diffusely reflected from the blood vessel can be normalized, so that changes in the image quality or brightness can be eliminated. The isosbestic wavelength measurement (FIG. 5C) allows measuring the total hemoglobin concentration. By performing these measurements at different wavelengths, the character of the oxygenation of the blood in the vessel can be obtained. The wavelengths chosen should be an isosbestic wavelength of the oxy- and deoxy-hemoglobin, such as that at 800 nm, or more preferably, as explained hereinabove, the isosbestic wavelength in the green region, at 570 nm, and two wavelengths, preferably on either side of the isosbestic point.

Figure 5E:
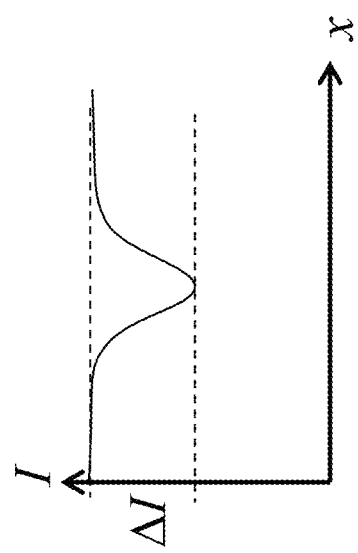
Figure 5F:
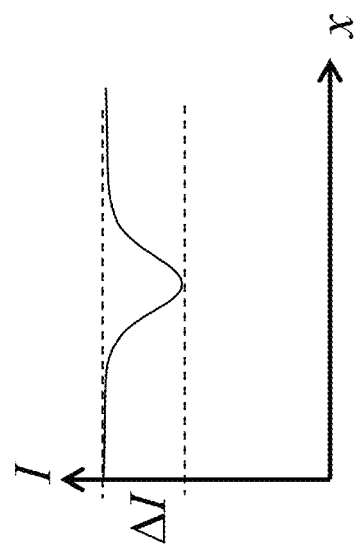
Figure 5G:
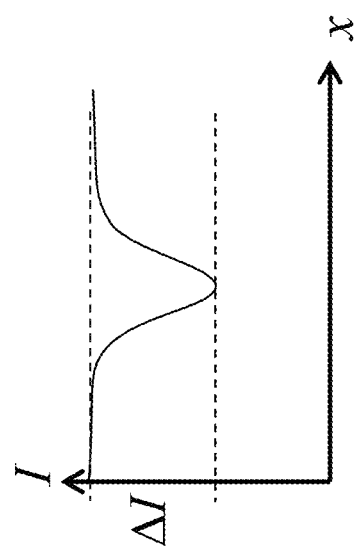

To illustrate this procedure, reference is now made to FIG. 5A, which shows a graph comparing absorption spectra for hemoglobin 500 and oxyhemoglobin 502, indicating an isosbestic wavelength, $\lambda_{isosbestic}$ and two wavelengths either side of the isosbestic wavelength. FIGS. 5B-D show three widefield images captured by camera 130 under illumination of different wavelengths. FIG. 5C shows a widefield image captured using the isosbestic wavelength $\lambda_{isosbestic}$ indicated in FIG. 5A, FIG. 5B shows a widefield image captured using a wavelength below $\lambda_{isosbestic}$, and FIG. 5D shows a widefield image captured using a wavelength above $\lambda_{isosbestic}$. The dashed lines across each image represent an imaging line along which the intensity profile of the vessel may be measured. Although images 5B-D differ in both brightness and contrast, they still indicate the absorption of the blood in the small vessel relative to its surrounding, as explained above. Thus, blood oxygenation of the blood vessel may be estimated by comparing FIGS. 5B-D, and the total hemoglobin concentration may be measured using FIG. 5C corresponding to $\lambda_{isosbestic}$. FIGS. 5E-G show absorption spectra for the blood vessel, corresponding varying illumination indicated for FIGS. 5B-D, respectively, where the vertical axis, indicated by I represents light intensity, and the horizontal axis, indicated by x represents the coordinate along the dashed lines in FIGS. 5B-D. As is evident from FIGS. 5B-D, the peak absorption levels shift when illuminated at wavelengths above, below and equal to $\lambda_{isosbestic}$, with the relative change $\Delta I$ in the imaged intensity of the vessel indicating the optical absorbance through the vessel. From the differences in $\Delta I$ at the three wavelengths measured, the ratio of the oxy- to deoxy-hemoglobin in the vessel can be obtained. The advantage of this method is that no spectrometric measurements need to be made on the images, the sequential illumination by the three wavelengths being sufficient to determine the oxygenation level and the total hemoglobin simply from the image processing of the separate vessel images captured by a simple camera.

The method of estimating the oxygenation and the total hemoglobin level is now explained. According to the modified Beer-Lambert law, light extinction after transmission through a region containing a vessel and the intervening tissue is given by:

$$A_{vessel}(\lambda) = [c_{Hb}\varepsilon_{Hb}(\lambda) + c_{HbO_2}\varepsilon_{HbO_2}(\lambda)] \cdot p_{vessel} + G_{tissue} \quad (1)$$

where A denotes the light extinction,
$\varepsilon$ is the molar extinction coefficient,
c is the substance molar concentration,
$p_{vessel}$ is the average optical path within the vessel, and
G is the signal loss due to scattering by the surrounding tissue.

Measuring light extinction at the tissue near the vessel, where there is no substantial absorption by blood absorption, only scattering by the tissue to a first approximation, and subtracting from the measurement of the extinction arising from the vessel yields:

$$A_{vessel}(\lambda) - A_{tissue}(\lambda) = [c_{Hb}\varepsilon_{Hb}(\lambda) + c_{HbO_2}\varepsilon_{HbO_2}(\lambda)] \cdot p_{vessel} \quad (2)$$

Without knowledge of $p_{vessel}$, only the relative concentration $c_{HbO_2}/(c_{HbO_2}+c_{Hb})$ can be calculated, providing the blood oxidization parameter. However, when $p_{vessel}$ is known, either by measurement or by estimation, it is possible to fit the measured absorption spectra using both concentration parameters and to obtain the total hemoglobin concentration:

$$c_{tot} = c_{Hb} + c_{HbO_2} \quad (3)$$

Using widefield images for hemoglobin measurement, the extinction difference for the isosbestic image is given by:

$$[A_{vessel} - A_{tissue}](\lambda_{iso}) = c_{tot} p_{vessel} \varepsilon_{HbO_2}(\lambda_{iso}) \quad (4)$$

since $\varepsilon_{Hb} = \varepsilon_{HbO_2}$ at the isosbestic wavelength. Therefore, if $p_{vessel}$ is known, either by calculation, or independent measurement, $c_{tot}$ may be calculated directly from Eq. (4) by comparing light extinctions in and nearby the vessel.

Medium sized vessels may be assumed to have a circular cross section, leading these vessels to appear darker at their center and brighter at the margins due to either the vessel having greater optical thickness at its center or alternatively, due to the higher concentration of blood flow at the center of the vessel. By assuming that the vessel has an approximately circular cross section, the true optical path length traveled by the light reaching the camera or the single detector can be computed. The true path-length is equal to the vessel diameter times the DPF (differential path-length factor). If there is no scattering, DPF=1. For large vessels, DPF can equal 2 or even more. The DPF can be predicted for different vessel sizes using numerical simulation or Monte Carlo light scattering simulations, or by measuring these effects on tissue models. The $p_{vessel}$ may thus be estimated or indirectly measured for every lateral location along the dashed lines in FIGS. 5B-D, corresponding to the peaks, valleys, and points of intersection of curves 500 and 502, to obtain $p_{vessel}(x)$. The total hemoglobin concentration $c_{tot}$ may then be estimated using a simple fit:

$$A_{vessel}(x) - A_{tissue} = c_{tot} \varepsilon_{HbO_2} p_{vessel}(x) \quad (5)$$

If the camera image is of high quality, the transverse profile of the dark vessel along the dashed lines in FIGS. 5B-5D, can assist in improving the accuracy, by using the extra data points along the vessel cross section, i.e. the darker center and brighter edges. Using the appropriate simulations, the single DPF value can then be replaced by a more complex analysis of the light emerging from the vessel. In this case, this is no longer a single path-length value and a single absorption measurement, but instead a more complex 2D/3D modeling of the vessel, combined with fitting the results to the 2D camera image.

The above described method may be performed on even small capillaries, provided that the camera has sufficient resolution. However there is a problem with very small capillaries, because of the nature of the spares blood flow through them, which may result in intermittent detection of clusters of red blood cells and their concomitant hemoglobin content. On the other hand, if the vessel selected is too large, the illuminating light may not penetrate through its entire depth, and provide an accurate reflection image of the conditions through the entire blood vessel. In order to overcome these two extreme situations, it is possible to select an area containing multiple vessels, of a size sufficiently small not to cause inaccuracy problems in the generation of the reflection image, and to perform the measurements sequentially on one vessel after the other, and to integrate the results to obtain an accurate measure of the total hemoglobin concentration.

One of the advantages of the above described methods of measuring the total hemoglobin level, is the comparative simplicity of the apparatus needed for such measurements. The apparatus need use only a few components and functions of the system shown in FIG. 2A. The illumination can be supplied by any suitable external source 102, and can be applied to the sample tissue by wide-field illumination in free-space. Instead of the spectrometer 114, a simple wavelength selection arrangement, such as a dichroic mirror or filter may be used to enable the optical measurements to be performed only at the isosbestic wavelength point, or close to it. The location and light detection of the region to be measured can be accomplished using a camera with resolution sufficient to image the blood vessels with the detail required to perform the above described image processing procedures. That camera may also be used in providing the images necessary for determining the optical path depth through the blood vessel. The camera may be equipped with a narrow-field confocal detection system to enable high resolution selection of the region to be imaged. The processor is adapted to perform the image analysis and compute the total hemoglobin content of the blood vessel, using the methods suggested by equations (1) to (5), and the calculation methods described in the previous two paragraphs of this disclosure. The system itself therefore becomes very simple in construction.

The above derivation has been described for a single isosbestic wavelength, but the optical measurement may also be obtained by using the previously described technique of multiple wavelengths and spectral analysis, thereby providing increased accuracy and the added information of an oxygenation determination. Additionally, although the full field examination and imaging provides a particularly simple method of performing the optical measurement, it is also possible to use a confocal method using a single point or small region measurement of the extinction at the blood vessel, together with a single point or small region reference measurement and the surrounding tissue.

Furthermore, the most accurate and the simplest method of implementing the above described methods and systems, are to perform the basic imaging of the blood vessel and its surrounding tissue at an isosbestic wavelength of oxyhemoglobin and deoxyhemoglobin, such that the effect of the oxygenation level of the blood is eliminated. This results in the simplest processing of the data, and the most accurate results. However it is also possible to operate the described methods and systems at a wavelength in the region of the isosbestic wavelength, where the difference in extinction coefficients of oxyhemoglobin and deoxyhemoglobin may be minimal, and the present disclosure is intended to cover such cases also. Furthermore, in situations where the oxygenation level of the patient is known, such as by use of a simple pulse oximetry measurement, since the spectral absorptions of oxyhemoglobin and deoxyhemoglobin are well known, it is possible to operate at a wavelength distant from an isosbestic point, and to use in the calculations based on the imaged intensities of the blood vessel and its surroundings, the extinction coefficients at that wavelength for the measured oxygenation level, and thus to derive the total hemoglobin level. As an even further method, it is possible to make an approximate estimate of the oxygenation level of the subject, based possibly on the clinical state of the subject, and to use that estimate in the derivation of the total hemoglobin calculation at any wavelength other than an isosbestic wavelength. For instance, it is known that in reasonably healthy subjects, an approximate level of oxygenation is of the order of 90% for an artery and 60% for a vein. However it is clear that any of these methods are likely to involve less accuracy than the previously described method using a measurement at or very close to an isosbestic wavelength.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for measuring total hemoglobin concentration in a blood vessel, comprising:
    illuminating a bodily tissue containing the blood vessel, using a specified illumination region;
    generating images of the blood vessel and its surrounding tissue, based on a specified light collection region, at a first wavelength in the region of an isosbestic wavelength of oxyhemoglobin and deoxy-hemoglobin;
    determining at that first wavelength, the comparative imaged intensities of the blood vessel and of the surrounding tissue;
    estimating the optical path length of the illumination through the vessel; and
    using the estimated optical path length and the comparative imaged intensities of the blood vessel and of the surrounding tissue to determine the total hemoglobin concentration in the blood flowing in the blood vessel,
    wherein a point spread function (PSF) of combined said specified illumination region and said specified light collection region has dimensions that are comparable to a cross-section of said blood vessel.

2. The method according to claim 1, wherein estimating the optical path length of the illumination through the vessel is obtained by determining the size of the vessel from at least one of the generated images.

3. The method according to claim 1, further comprising:
    generating images of the blood vessel and its surrounding tissue at at least one additional wavelength in proximity to the first wavelength;
    determining the comparative imaged intensities of the blood vessel at the first wavelength and at the at least one additional wavelength in proximity thereto; and
    using the comparative imaged intensities of the blood vessel to determine the oxygen absorption level in the blood.

4. The method of claim 3, wherein the at least one additional wavelength is a range of multiple wavelengths.

5. A method according to claim 1, wherein the images of the blood vessel and its surrounding tissue are obtained from a camera system.

6. A method according to claim 1, wherein the images of the blood vessel and its surrounding tissue are obtained from a narrow field confocal microscope system.

7. The method according to claim 1, wherein the first wavelength images are generated by illuminating at the first wavelength.

8. The method according to claim 1, wherein the first wavelength images are generated by imaging at the first wavelength.

9. A system for measuring total hemoglobin concentration in a blood vessel, comprising:
    a light source configured to illuminate the blood vessel and its surrounding tissue, using a specified illumination region;
    a camera configured to generate images of the blood vessel and its surrounding tissue, based on a specified light collection region, at a first wavelength in the region of an isosbestic wavelength of oxyhemoglobin and deoxy-hemoglobin; and
    a processor configured to:
    (a) determine from at least one of the images generated at the first wavelength, the comparative imaged intensities of the blood vessel and of the surrounding tissue;
    (b) estimate the optical path length of the illumination through the blood vessel; and
    (c) use the estimated optical path length and the comparative imaged intensities of the blood vessel and of the surrounding tissue to determine the total hemoglobin concentration in the blood flowing in the blood vessel
    wherein a point spread function (PSF) of combined said specified illumination region and said specified light collection region has dimensions that are comparable to a cross-section of said blood vessel.

10. The system of claim 9, wherein estimating the optical path length of the illumination through the blood vessel is obtained by determining the size of the vessel from at least one of the generated images.

11. A system according to claim 9, wherein the camera is configured to generate images of the blood vessel and its surrounding tissue at at least one additional wavelength in proximity to the first wavelength; and
    wherein the processor is further configured to
    (d) determine the comparative imaged intensities of the blood vessel at the first wavelength and at the at least one additional wavelength in proximity thereto; and
    (e) use the comparative imaged intensities of the blood vessel to determine the oxygen absorption level in the blood.

12. The system of claim 11, wherein the at least one additional wavelength is a range of multiple wavelengths.

13. A system according to claim 9, wherein the light source is configured to provide wide field illumination.

14. A system according to claim 9, wherein the camera comprises a confocal microscope system configured to image the blood vessel and its surrounding tissue.

15. A system according to claim 9, wherein the first wavelength images are generated by illuminating at the first wavelength.

16. A system according to claim 15, wherein said illuminating is provided by said light source.

17. A system according to claim 9, wherein the first wavelength images are generated by at least one filter disposed in the optical path of the illumination either before incidence on the blood vessel and its surrounding tissue, or after reflection from the blood vessel and its surrounding tissue.

* * * * *